(12) United States Patent
Tonkovich et al.

(10) Patent No.: US 7,999,144 B2
(45) Date of Patent: Aug. 16, 2011

(54) MICROCHANNEL APPARATUS AND METHODS OF CONDUCTING CATALYZED OXIDATIVE DEHYDROGENATION

(75) Inventors: Anna Lee Tonkovich, Dublin, OH (US); Bin Yang, Columbus, OH (US); Steven T. Perry, Galloway, OH (US); Terry Mazanec, Solon, OH (US); Ravi Arora, New Albany, OH (US); Francis P. Daly, Delaware, OH (US); Richard Long, New Albany, OH (US); Thomas D. Yuschak, Lewis Center, OH (US); Paul W. Neagle, Westerville, OH (US); Amanda Glass, Galloway, OH (US)

(73) Assignee: Velocys, Plain City, OH (US)

( * ) Notice: Subject to any disclaimer, the term of this patent is extended or adjusted under 35 U.S.C. 154(b) by 1245 days.

(21) Appl. No.: 11/469,847

(22) Filed: Sep. 1, 2006

(65) Prior Publication Data
US 2008/0058574 A1  Mar. 6, 2008

(51) Int. Cl.
*C07C 5/32* (2006.01)
(52) U.S. Cl. ........ 585/658; 585/654; 585/656; 585/659; 585/660; 585/435; 585/440; 585/441; 585/443; 585/444; 422/601; 422/603
(58) Field of Classification Search .................. 585/658, 585/654, 656
See application file for complete search history.

(56) References Cited

U.S. PATENT DOCUMENTS

| | | | |
|---|---|---|---|
| 3,944,505 A | 3/1976 | LaCroix | |
| 4,524,236 A | 6/1985 | McCain | |
| 4,739,124 A | 4/1988 | Ward | |
| 4,760,210 A | 7/1988 | Sweeney | |
| 4,940,826 A | 7/1990 | Font Freide et al. | |
| 5,254,788 A | 10/1993 | Gartside et al. | |
| 5,563,314 A * | 10/1996 | Agaskar et al. | 585/654 |
| 5,593,935 A | 1/1997 | Golunski et al. | |
| 5,625,111 A * | 4/1997 | Astbury et al. | 585/653 |
| 5,639,929 A | 6/1997 | Bharadwaj | |
| 5,811,062 A | 9/1998 | Wegeng et al. | |
| 5,935,489 A | 8/1999 | Hershkowitz et al. | |
| 5,997,826 A | 12/1999 | Lodeng et al. | |
| 6,117,578 A | 9/2000 | Lesieur | |
| 6,166,283 A | 12/2000 | Bharadwaj | |
| 6,190,624 B1 | 2/2001 | Romantier | |
| 6,207,128 B1 * | 3/2001 | Sellin et al. | 423/588 |
| 6,274,113 B1 | 8/2001 | Heyse et al. | |

(Continued)

FOREIGN PATENT DOCUMENTS

| | | |
|---|---|---|
| WO | WO 01/12312 | 2/2001 |
| WO | WO 01/54807 | 8/2001 |
| WO | WO 2004108639 A1 * | 12/2004 |

OTHER PUBLICATIONS

PCT Written Opinion in PCT/US2005/009814, mailed Oct. 5, 2006.

(Continued)

*Primary Examiner* — Glenn A Caldarola
*Assistant Examiner* — Bradley Etherton
(74) *Attorney, Agent, or Firm* — Frank Rosenberg

(57) ABSTRACT

Methods of oxidative dehydrogenation are described. Surprisingly, Pd and Au alloys of Pt have been discovered to be superior for oxidative dehydrogenation in microchannels. Methods of forming these catalysts via an electroless plating methodology are also described. An apparatus design that minimizes heat transfer to the apparatus' exterior is also described.

30 Claims, 15 Drawing Sheets

U.S. PATENT DOCUMENTS

| | | | |
|---|---|---|---|
| 6,315,977 B1 | 11/2001 | Cantacuzene | |
| 6,365,543 B1 | 4/2002 | Schmidt et al. | |
| 6,452,061 B1 * | 9/2002 | Schmidt et al. | 585/658 |
| 6,488,838 B1 | 12/2002 | Tonkovich et al. | |
| 6,515,146 B1 | 2/2003 | Perregaard et al. | |
| 6,566,573 B1 * | 5/2003 | Bharadwaj et al. | 585/658 |
| 6,709,640 B1 | 3/2004 | Romantier et al. | |
| 6,746,651 B1 * | 6/2004 | Ponzo et al. | 422/220 |
| 6,756,340 B2 | 6/2004 | Voskoboynikov et al. | |
| 6,756,515 B2 | 6/2004 | Rende et al. | |
| 6,846,773 B1 | 1/2005 | Yokoyama et al. | |
| 7,402,719 B2 | 7/2008 | Brophy et al. | |
| 2003/0007904 A1 | 1/2003 | Tonkovich et al. | |
| 2003/0094381 A1 | 5/2003 | Bors et al. | |
| 2003/0116503 A1 | 6/2003 | Wang et al. | |
| 2004/0034266 A1 * | 2/2004 | Brophy et al. | 585/658 |
| 2004/0220434 A1 | 11/2004 | Brophy et al. | |
| 2005/0272965 A1 | 12/2005 | Watson et al. | |
| 2008/0031788 A1 | 2/2008 | Brophy et al. | |
| 2009/0004076 A1 | 1/2009 | Brophy et al. | |
| 2009/0012341 A1 | 1/2009 | Brophy et al. | |

OTHER PUBLICATIONS

Bhasin et al., "Dehydrogenation and oxydehydrogenation of paraffins to olefins," Appl. Catal. A, Gen. 221 (2001) 397-419.

Wolfrath et al., "Novel Membrane Reactor with Filamentous Catalytic Bed for Propane Dehydrogenation," Ind. Eng. Chem. Res. 2001, 40. 5234-5239.

Kestenbaum et al., "Synthesis of ethylene oxide in a microreaction system," in IMRET 3 Proceedings of the Third international Conf. on Microreaction Technology 207-212 (1999).

Beretta et al., "Production of olefins via oxidative dehydrogenation of light paraffins at short contact times," Catalysis Today, 64, pp. 103-111 (2001).

Steinfeldt et al., "Comparative studies of the oxidative dehydrogenation of propane in micro-channels reactor module and fixed-bed reactor," Studies in Surface Science and Catalysis, pp. 185-190 (2001).

Claus et al., "Miniaturization of screening devices for the combinatorial development of heterogensous catalysts," Catalysis Today, 67, pp. 319-339 (2001).

* cited by examiner

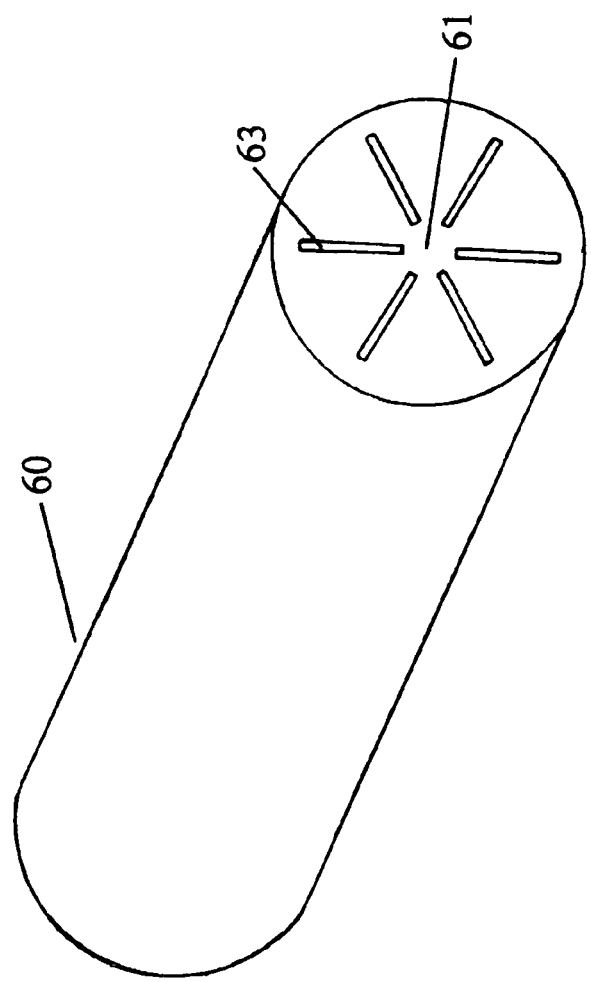

MICROCHANNEL APPARATUS AND METHODS OF CONDUCTING CATALYZED OXIDATIVE DEHYDROGENATION

GOVERNMENT RIGHTS

This invention was made with Government support under contract # DE-FC36-04GO14154 awarded by the United States Department of Energy. The government has certain rights in the invention.

BACKGROUND OF THE INVENTION

Oxidative dehydrogenation (ODH) has for a long period been a topic on intense academic and industrial interest due to its potential for economically producing olefins. One promising route to oxidative dehydrogenation is by utilizing the advantages provided by microchannel technology. Pioneering work in designing microchannel systems for oxidative dehydrogenation is described in U.S. Published Patent Application No. 2004/0034266 by Brophy et al., and this published application is incorporated herein as if reproduced in full below. Improved catalyst formulations and methods for conducting ODH in microchannels are described in U.S. Published Patent Application No. 20050272965, published Dec. 8, 2005; this published application is also incorporated herein as if reproduced in full below.

Numerous types of conventional apparatus have been proposed for conducting ODH reactions including monoliths, fixed beds and fluidized beds. Lodeng et al. in U.S. Pat. No. 5,997,826 describe a reaction in which relatively narrow, catalyst-free oxygen mixing zones alternate with relatively larger catalyst-containing ODH zones.

Pt and some Pt alloys have long been known as catalysts for some applications in high temperature oxidative dehydrogenation. For example, Font Freide et al. in U.S. Pat. No. 4,940,826 discuss Pt and Pt—Pd catalysts for the oxidative dehydrogenation of ethane, propane and butane. U.S. Pat. Nos. 5,639,929 and 6,846,773 report the use of Pt—Au catalyst particles in fluidized bed reactors, although in the '773 patent it is mentioned that a Pt—Au monolith catalyst could not initiate ethane ODH. Although several patents broadly discuss a broad range of Pt catalysts; recent work have focused on Pt—Sn and Pt—Cu as the best catalysts for ODH. See U.S. Pat. Nos. 6,166,283, 6,365,543, 6,566,573, 6,756,515, and 6,756,340. Indeed, Schmidt et al. (see, for example, U.S. Pat. No. 6,452,061) have warned against Pd or Au alloys with Pt because these alloys are detrimental to the results of the ODH process.

SUMMARY OF THE INVENTION

The invention provides novel methods of oxidatively dehydrogenating a hydrocarbon. Novel apparatus and systems are also disclosed.

In a first aspect, the invention provides a method for oxidatively dehydrogenating a hydrocarbon, comprising: passing a an oxygen source and a hydrocarbon into a microchannel at a temperature of at least 850° C. The microchannel comprises an electroless plating of a Pt alloy catalyst wherein the Pt alloy comprises Au or Pd as an alloying element. In this method, the flow rate is controlled such that the contact time is 100 ms or less. In this method, at least 70% of the hydrocarbon is converted to products, selectivity to alkene or aralkene is at least 80%; and conversion and selectivity are maintained above these levels for at least 100 hours without performing a decoking step or a catalyst regeneration step.

In another aspect, the invention provides a method for oxidatively dehydrogenating a hydrocarbon, comprising: passing a process stream comprising an oxygen source and a hydrocarbon into a microchannel in a first section of a microchannel reactor, wherein, in the first section, the oxygen reacts with a fuel to generate heat; flowing the feed stream through a u-bend and into a second section; wherein the first section, in a region where the oxygen source reacts with the fuel to generate heat, comprises a first cross-sectional area; wherein the process stream in the first section and a process stream in a second section are separated by a thermally conductive wall; wherein heat from the reaction with oxygen in the first section passes through the thermally conductive wall and into the process stream in the second section; and, in the second section, removing hydrogen from the hydrocarbon to form a product and hydrogen; wherein the second section comprises a second cross-sectional area; and wherein the second cross sectional area is at least twice as large as the first cross-sectional area.

In a further aspect, the invention provides a method for oxidatively dehydrogenating a hydrocarbon, comprising: passing a process stream comprising an oxygen source and a hydrocarbon into a microchannel in a first section of a microchannel reactor, wherein the microchannel reactor comprises a continuous flow path through the first section, into and through a second section; wherein, in the first section, the oxygen source reacts with a fuel to generate heat; wherein the first section, in a region where the oxygen source reacts with the fuel to generate heat, includes a first cross-sectional area. The process stream passes from the first section into the second section; and, in the second section, the hydrocarbon reacts to form an alkene or aralkene and hydrogen; wherein the second section comprises a second cross-sectional area. In this method, the second cross sectional area is at least three times as large as the first cross-sectional area; and the continuous flow path comprises a transitional region from the first cross-sectional area to the second cross-sectional area, wherein the transitional region comprises an increasing cross-sectional area that increases in cross-sectional area from the first cross-sectional area to the second cross-sectional area, and the transitional region does not contain any region in which the flow path increases in cross-sectional area by three times or more over a length less than 0.6 cm, except that, if the transitional region includes a u-bend, there can be a region within 1 cm of the u-bend in which the flow path increases in cross-sectional area by three times or more over a length less than 0.6 cm. By use of this method, coking in the reactor can be eliminated or greatly reduced.

In yet another aspect, the invention provides chemical processing apparatus, comprising: a processor body having a length and comprising a central axis and at least two flow paths along a length of the processor body and radiating out from the center axis; wherein, in a direction perpendicular to length, each of the at least two flow paths have a cross section that is substantially rectangular. Here "radiating out" does not mean that the paths necessarily touch the center axis, only that the width of the paths project in a radial direction away from the central axis. "Length" is perpendicular to width and length of the processor body is defined to be in same direction as the length of the flow paths which are substantially straight. The invention also includes a method using this apparatus to conduct one or more unit operations in the flow paths. A preferred unit operation is ODH. Preferably, the processor body is cylindrical.

In a further aspect, the invention provides a method for oxidatively dehydrogenating a hydrocarbon, comprising: passing a process stream comprising an oxygen source and a hydrocarbon into a microchannel in a first section of a microchannel reactor, wherein, in the first section, the oxygen source reacts with a fuel to generate heat. The first section includes a Pt alloy catalyst that comprises Au or Pd as an alloying element. The process stream flows through a u-bend and into a second section. The process stream in the first section and a process stream in a second section are separated by a thermally conductive wall. Heat from the reaction with oxygen in the first section passes through the thermally conductive wall and into the process stream in the second section; and, in the second section, the hydrocarbon reacts to form a product and hydrogen. In this method, heat from the oxidation reaction typically passes into the product (second) section by both convection and conduction through the thermally conductive wall.

In another aspect, the invention provides a method for oxidatively dehydrogenating a hydrocarbon, comprising: passing a process stream comprising an oxygen source and a hydrocarbon into a microchannel in a first section of a microchannel reactor, wherein, in the first section, the oxygen source reacts with a fuel to generate heat. The process stream flows through a u-bend and into a second section. The process stream in the first section and a process stream in a second section are separated by a thermally conductive wall; and heat generated by the reaction of fuel with the oxygen source in the first section passes through the thermally conductive wall and into the process stream in the second section. In the second section, the hydrocarbon reacts to form a product and hydrogen. In this method, more of the product (alkene or aralkene) is formed in the second section than in the first section.

The invention also includes catalysts comprising a Pt alloy disposed on a substrate, where the Pt alloy comprises Pt alloyed with Pd and/or Au. Preferably, the Pt alloy is formed by electroless plating—the electroless plating technique yields a unique structure that is not obtained with other techniques. Preferably the substrate comprises an aluminide layer. The catalyst may additionally be characterized by any of the properties (including reactive properties) disclosed in the specification or examples. For example, the catalyst can be characterized as possessing an activity such that, when exposed to the conditions of example 1 (or any of the other examples), at 902° C., there is an ethane conversion of at least 70%, preferably at least 75%, and a selectivity of at least 80% for at least 100 hours.

The invention further includes any of the apparatus described here. In particular, the invention includes any of the apparatus described in conjunction with the inventive methods. Any of the devices described here will often be integrated within a larger device. For example, the process channel will typically include a run up length in which there is little or no reaction occurs (which could be due to low temperature or lack of an oxygen source); and the run up length of the process channel is adjacent to an extended length of product channel. In this region, which is prior to the first section where oxidation occurs and typically after the majority of the second section where dehydrogenation occurs, there is thermal transfer from the hot product stream to the cooler process stream in the run up to the oxidation section.

The invention also includes systems having the characteristics described herein. Systems of the invention can be described as including apparatus and/or catalyst in combination with reactants and/or products. Optionally, systems can be further characterized by the conditions at which they operate.

GLOSSARY

In some preferred embodiments, the internal surfaces have been coated with a metal aluminide, which is typically itself coated with one or more layers, such as a catalyst layer. "Metal aluminide" refers to a metallic material containing 10% or more Metal and 5%, more preferably 10%, or greater Aluminum (Al) with the sum of Metal and Al being 50% or more. These percentages refer to mass percents. Preferably, a metal aluminide contains 50% or more metal and 10% or greater Al with the sum of Ni and Al being 80% or more. In embodiments in which Metal and Al have undergone significant thermal diffusion, it is expected that the the composition of a Metal-Al layer will vary gradually as a function of thickness so that there may not be a distinct line separating the Metal-Al layer from an underlying Metal-containing alloy substrate. A preferred metal aluminide is nickel aluminide (NiAl). "Nickel aluminide" refers to a material containing 10% or more Ni and 10% or greater Al with the sum of Ni and Al being 50% or more. These percentages refer to mass percents. Preferably, a nickel aluminide contains 20% or more Ni and 10% or greater Al with the sum of Ni and Al being 80% or more. In embodiments in which Ni and Al have undergone significant thermal diffusion, it is expected that the composition of a Ni—Al layer will vary gradually as a function of thickness so that there may not be a distinct line separating the Ni—Al layer from an underlying Ni-based alloy substrate. Microchannel apparatus having metal aluminide coatings are described elsewhere, and, therefore, they are not described in detail here.

A "catalyst material" is a material that catalyzes a desired reaction. It is not simply alumina. A catalyst material "disposed over" a layer can be a physically separate layer (such as a sol-deposited layer) or a catalyst material disposed within a porous, catalyst support layer. "Disposed onto" or "disposed over" mean directly on or indirectly on with intervening layers. In some preferred embodiments, the catalyst material is directly on a thermally-grown alumina layer, meaning without any intervening layers.

A "catalyst metal" is the preferred form of catalyst material and is a material in metallic form that catalyzes a desired reaction.

A "chemical unit operation" comprises reactions, separations, heating, cooling, vaporization, condensation, and mixing.

As is conventional patent terminology, "comprising" means including and when this term is used the invention can, in some narrower preferred embodiments, be described as "consisting essentially of" or in the narrowest embodiments as "consisting of." Aspects of the invention described as "comprising a" are not intended to be limited to a single component, but may contain additional components. Compositions "consisting essentially of" a set of components allow other components that so not substantially affect the character of the invention, and, similarly, compositions that are "essentially" without a specified element do not contain amounts of the element as would substantially affect the desired properties. In place of "comprising", any of the terms "consists of" or "consists essentially of", may alternatively be used to describe more limited aspects of the invention.

Unless stated otherwise, "conversion percent" refers to absolute conversion percent throughout these descriptions. "Contact time" is defined as the total catalyst chamber volume (including the catalyst substrate volume) divided by the total volumetric inlet flowrate of reactants at standard temperature and pressure (STP: 273K and 1.013 bar absolute). Catalyst chamber volume includes any volume between a catalyst coating (or other flow-by catalyst arrangement) and the opposite wall of a reaction channel.

In preferred embodiments, an electroless coating is contiguous over at least 1 cm, more preferably at least 5 cm, of a microchannel.

The phrase a "coating grows away from the wall" refers to the direction that a coating grows—either by thermal oxidation or an accretion process such as electroless plating.

A "contiguous microchannel" is a microchannel enclosed by a microchannel wall or walls without substantial breaks or openings—meaning that openings (if present) amount to no more than 20% (in some embodiments no more than 5%, and in some embodiments without any openings) of the area of the microchannel wall or walls on which the opening(s) are present.

"Directly disposed" means that a material is directly applied to a specified layer. There is not an intervening washcoating, nor is the material codeposited with a washcoated catalyst support. "Directly deposited" has the same meaning. The inventive method is very flexible, an electroless catalyst layer can be directly deposited electrolessly on any of the substrates mentioned herein.

"Hydrocarbon" is any alkane or aralkane containing from 2 to 20 carbon atoms.

An "interior microchannel" is a microchannel within a device that is surrounded on all sides by a microchannel wall or walls except for inlets and outlets, and, optionally, connecting holes along the length of a microchannel such as a porous partition or orifices such as connecting orifices between a fuel channel and an oxidant channel. Since it is surrounded by walls, it is not accessible by conventional lithography, conventional physical vapor deposition, or other surface techniques.

An "insert" is a component that can be inserted into a channel.

A "manifold" is a header or footer that connects plural microchannels and is integral with the apparatus.

Measurement techniques—For all coatings, "average thickness" can be measured by cross-sectional microscopy (obtained by cutting open a microchannel device) or, for coatings that are about 5 µm thick or less, by EDS elemental analysis. In the case of channels connected to a common manifold or otherwise connected to be filled from the same inlet, the "average thickness" is averaged over all the channels, or for a large number of connected channels, at least 10 channels selected to fairly represent the totality of the connected channels. Measurements should be made over the entire length of a contiguous coating; that is, not just for 1 cm selected out of a larger contiguous coating. "Coating loading" is measured the same as average thickness except that height and/or thickness (or elemental analysis) of the coating is measured to get a volume or mass. Unless specified as a corner measurement, average coating thickness should be measured along the center line between corners (if present), and any set of corners can be selected. Corner thickness can be measured on a single corner; however, the corner must be representative (not an aberration).

A "microchannel" is a channel having at least one internal dimension (wall-to-wall, not counting catalyst) of 1 cm or less, preferably 2 mm or less (in some embodiments about 1.0 mm or less) and greater than 100 nm (preferably greater than 1 µm), and in some embodiments 50 to 500 µm. Microchannels are also defined by the presence of at least one inlet that is distinct from at least one outlet. Microchannels are not merely channels through zeolites or mesoporous materials. The length of a microchannel corresponds to the direction of flow through the microchannel. Microchannel height and width are substantially perpendicular to the direction of flow of through the channel. In the case of a laminated device where a microchannel has two major surfaces (for example, surfaces formed by stacked and bonded sheets), the height is the distance from major surface to major surface and width is perpendicular to height.

"Ni-based" alloys are those alloys comprising at least 30%, preferably at least 45% Ni, more preferably at least 60% (by mass). In some preferred embodiments, these alloys also contain at least 5%, preferably at least 10% Cr.

A "post-assembly" coating is applied onto three dimensional microchannel apparatus. This is either after a laminating step in a multilayer device made by laminating sheets or after manufacture of a manufactured multi-level apparatus such as an apparatus in which microchannels are drilled into a block. This "post-assembly" coating can be contrasted with apparatus made by processes in which sheets are coated and then assembled and bonded. The post-assembly coating provides advantages such as crack-filling and ease of manufacture. Additionally, a coating could interfere with diffusion bonding of a stack of coated sheets and result in an inferior bond. Whether an apparatus is made by a post-assembly coating is detectable by observable characteristics such as gap-filling, crack-filling, elemental analysis (for example, elemental composition of sheet surfaces versus bonded areas). Typically, these characteristics are observed by optical microscopy, electron microscopy or electron microscopy in conjunction with elemental analysis. Thus, for a given apparatus, there is a difference between pre-assembled and post-assembled coated devices, and an analysis using well-known analytical techniques can establish whether a coating was applied before or after assembly (or manufacture in the case of drilled microchannels) of the microchannel device. In preferred embodiments, an electroless plating is applied post-assembly.

"Unit operation" means chemical reaction, vaporization, compression, chemical separation, distillation, condensation, mixing, heating, or cooling. A "unit operation" does not mean merely fluid transport, although transport frequently occurs along with unit operations. In some preferred embodiments, a unit operation is not merely mixing.

BRIEF DESCRIPTION OF THE DRAWINGS

FIG. 6a-c shows an embodiment of apparatus that minimizes heat transfer to the exterior of the device. FIG. 6a shows, in cross-section, the flow path slots. FIG. 6b is a cut away view of a u-bend.

FIG. 6c is a scaled up device with multiple units.

DETAILED DESCRIPTION OF THE INVENTION

Catalysts

Figure 1:
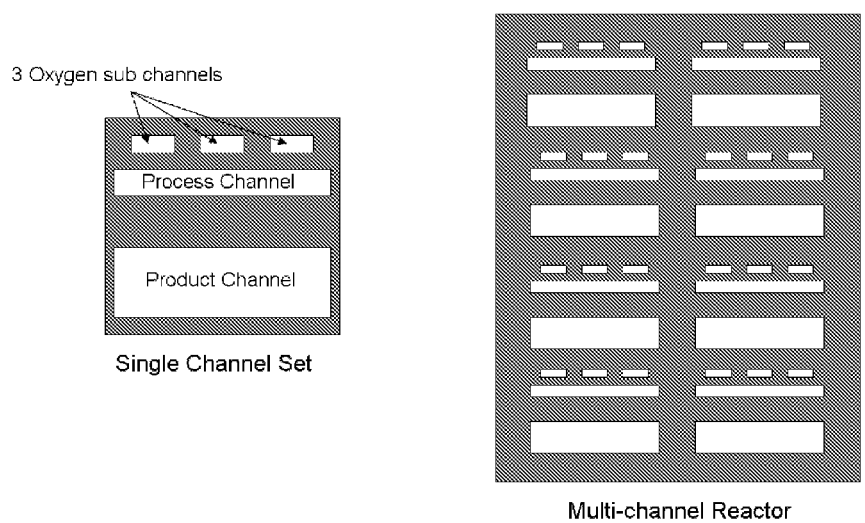
FIG. 1 is a cross-sectional (cut away) view of apparatus for ODH that was modeled in the Examples section.

As is known, an electroless plating solution comprises a metal compound and a reducing chemical. A complexing agent may be added to prevent reduction of the metal ions in solution. In some embodiments, the reduction process may be catalyzed by a small amount of catalytic metal ions. Preferred metals for the electroless deposition include Cu, Au, Pd, Pt, Sn and combinations thereof. After plating, the residual solution could be drained out.

The use of electroless plating of catalytic metals on reactor walls, both conductive and non-conductive, can be used to create a uniform metal coating inside a channel. Such an electroless plating solution could comprise a water soluble metal salt, a reducing agent such as hydrazine hydrate, possibly a stabilizer such as EDTA to prevent precipitation of the plating metal, optionally an accelerator such as 3,4-dimethoxybenzoic acid or an acid such as acetic acid to adjust the pH for optimum plating. For a microchannel reactor the electroless plating solution is preferably filled (to the desired height) within the channels prior to the initiation of the reaction. Pressure can be applied during filling to control fill height in selected channels. The solution could be introduced at room temperature or below and then heated to the requisite plating temperature. In some applications it may be important that the plating process end before the plating solution is drained, particularly if the draining process is long relative to the plating process, to achieve a uniform coating. This can be accomplished by, for example, controlling a plating composition/reaction in which one of the essential reactants is depleted before the draining process begins. Another approach would be to reduce the plating temperature prior to draining. For example, in addition to the draining issues, the plating liquid should be selected to be stable in microchannels so that particles will not form in solution and drift by gravity.

In this invention, we have found that the Pt alloys (e.g., Pt—Cu, Pt—Au and Pt—Pd) prepared with electroless plating exhibit surprisingly superior ODH performance. The superior performance may be due to better coating uniformity and better heat transfer. For electroless plating of alloys, the substrates could be plated with Pt first, or another metal first, or two or more metals simultaneously. The Pt/metal ratio and total loading could be controlled by plating conditions, such as temperature, solution concentration, and plating time. Preferred Pt alloys could include Pt—Cu, Pt—Au, Pt—Ag, Pt—Pd, Pt—Fe, Pt—Co, Pt—Ni, and combinations thereof. Additional promoters, stabilizing materials, or chemical modifiers, or combinations of these could be included. Examples of these include transition metal ions especially Group 8 ions, alkali or alkaline earth elements, lanthanides or rare earth elements, or combinations of these. These additional materials could be added before or after the precious metals. After Pt and metal plating, the catalysts could be heat-treated at high temperatures to form Pt alloys. The heat-treating atmosphere could be oxidizing, reducing, or inert atmosphere or in vacuum.

The metal content in a catalyst or other article can be described either in terms of weight percent or in terms of mass per geometric surface area of substrate. Weight percent is based on the weight of platinum (in preferred ODH catalysts) as a percent of catalyst powder, catalyst pellets, or washcoat; it does not include the weight of an underlying substrate and does not include the weight of interlayers between a washcoat (or washcoats) and an underlying substrate. For example, in the case of an alloy felt washcoated with alumina and Pt, the weight % would be $Pt/(Pt+Al_2O_3) \times 100\%$. For a metal coupon that has been aluminized, then oxidized, then treated with solution of alumina and lanthanum and Pt, the weight of the oxidized aluminized layer would not be included in the calculation of weight % Pt.

For flat or substantially flat substrates (such as a flat microchannel wall), a coating can be characterized by the amount of desired material on a geometric surface area; that is, an area that can be measured with a ruler. For purposes of the present invention, a microchannel wall with embedded surface features is considered a substantially flat surface. In some preferred embodiments, the catalyst contains at least 0.3 mg/cm$^2$ Pt, in some preferred embodiments at least 0.6 mg/cm$^2$ Pt, and in some embodiments 0.2 to 2 mg/cm$^2$ Pt. For purposes of this measurement, the area refers to the geometrical area of the substrate; for a flat surface such as a foil or coupon, this area is quite simple, for a honeycomb or finned substrate or reaction channel, it would include all the surfaces that are coated by catalyst. The weight percent of Pt can be determined by known methods of chemical analysis.

Preferred catalyst compositions comprise Pt alloyed with Au and/or Pd. The effectiveness of these catalysts was surprising in view of the prior art teachings that these alloys would be plagued by coking problems. Gold (Au), if present, is preferably present in a Pt:Au ratio of 10:1 to 0.5:1, more preferably about 3:1 to about 1:1, more preferably 2.5:1 to 1.5:1, and in some embodiments about 2:1. Palladium (Pd), if present, is preferably in the present in a Pt:Au ratio of up to about 10:1, more preferably 5:1 to 0.5:1, and still more preferably 1.5:1 to 0.5:1, and in some embodiments about 1:1. Gold is superior to tin because it is less volatile.

Unless otherwise specified, elemental analyses of wall coatings should be determined using energy dispersive spectroscopy (EDS) at 20 kV excitation energy (at 100×, or if 100× is larger than the area available, then the largest available area for SEM, recognizing that some modifications may be required if such measurement conditions are impracticable for particular systems). As is well-known, this technique measures the surface composition, as well as some thickness below the surface. Some catalysts of this invention have a surface area, as measured by $N_2$ adsorption BET, of 10 m$^2$/g or less, and in some embodiments a surface area of 5 m$^2$/g or less.

A catalyst coating can be applied to any support, including pellets, foams and honeycombs, and, in preferred embodiments is applied to a microchannel wall.

Thermally Grown Oxide

Prior to electroless plating, an oxide layer may be formed by exposing a surface to an oxidizing atmosphere at elevated temperature. In some preferred embodiments, a nickel aluminide or platinum aluminide layer is oxidized. The thermally-grown oxide layer is preferably 10 µm thick or less, more preferably 1 µm thick or less, and in some embodiments is 0.2 µm to 5 µm thick. Typically, these thicknesses are measured with an optical or electron microscope. Generally, the thermally-grown oxide layer can be visually identified; the underlying aluminide layer is metallic in nature and contains no more than 5 wt % oxygen atoms; surface washcoat layers may be distinguished from the thermally-grown oxide by differences in density, porosity or crystal phase.

It should be recognized that the term "alumina" can be used to refer to a material containing aluminum oxides in the presence of additional metals. In the descriptions herein, unless specified, the term "alumina" encompasses substantially pure material ("consists essentially of alumina") and/or aluminum oxides containing modifiers.

Surface Features in Microchannel Walls

In some preferred embodiments, apparatus contains channels having surface features to enhance fluid contact with a catalyst and/or channel walls. Surface features are protrusions from or recesses into a channel wall. If the area at the top of the features is the same or exceeds the area at the base of the feature, then the feature may be considered recessed. If the area at the base of the feature exceeds the area at the top of the feature, then it may be considered protruded. Surface features are described in detail in U.S. patent application Ser. No. 11/388,792, filed Mar. 23, 2006, which is incorporated herein as if reproduced in full below. The staggered herringbone configuration is a particularly well-known configuration for surface features.

Preferred ranges for surface feature depth (as defined as recessed or protruded distance normal to the direction of flow through a channel) are less than 2 mm. More preferably less than 1 mm. In some embodiments from 0.01 mm to 0.5 mm. The preferred range for the width of the surface feature (as defined as the open distance parallel to the direction of gravity) is less than 2 mm. More preferrably less than 1 mm. In some embodiments from from 0.1 to 0.5 mm.

An advantage of electroless plating is that essentially uniform coatings can be formed on surface features within a microchannel. Measuring coating thickness can be performed ex situ by cutting the device into cross sections and taking SEM photographs to quantitatively measure the coating thickness.

Microchannel Apparatus

Microchannel reactors are characterized by the presence of at least one reaction channel having at least one dimension (wall-to-wall, not counting catalyst) of 1.0 cm or less, preferably 2.0 mm or less (in some embodiments about 1.0 mm or less) and greater than 100 nm (preferably greater than 1 µm), and in some embodiments 50 to 500 µm. A reaction channel is a channel containing a catalyst. Microchannel apparatus is similarly characterized, except that a catalyst-containing reaction channel is not required. Both height and width are substantially perpendicular to the direction of flow of reactants through the reactor. Microchannels are also defined by the presence of at least one inlet that is distinct from at least one outlet—microchannels are not merely channels through zeolites or mesoporous materials. The height and/or width of a reaction microchannel is preferably about 2 mm or less, and more preferably 1 mm or less. The length of a reaction channel is typically longer. Preferably, the length of a reaction channel is greater than 1 cm, in some embodiments greater than 20 cm, and in some embodiments in the range of 1 to 100 cm. The sides of a microchannel are defined by reaction channel walls. These walls are preferably made of a hard material such as a ceramic, an iron based alloy such as steel, or a Ni—, Co— or Fe-based superalloy such as monel. The choice of material for the walls of the reaction channel may depend on the reaction for which the reactor is intended. In some embodiments, the reaction chamber walls are comprised of a stainless steel or Inconel® or other high temperatre alloy which is durable and has good thermal conductivity. Typically, reaction channel walls are formed of the material that provides the primary structural support for the microchannel apparatus. Some microchannel apparatus includes at least 10 layers laminated in a device, where each of these layers contain at least 10 channels; the device may contain other layers with less channels.

Microchannel reactors preferably include a plurality of microchannel reaction channels and may also contain a plurality of adjacent heat exchange microchannels. The plurality of microchannel reaction channels may contain, for example, 2, 10, 100, 1000 or more channels. In preferred embodiments, the microchannels are arranged in parallel arrays of planar microchannels, for example, at least 3 arrays of planar microchannels. In some preferred embodiments, multiple microchannel inlets are connected to a common header and/or multiple microchannel outlets are connected to a common footer. Pressure drops can be low, allowing high throughput and the catalyst can be fixed in a very accessible form within the channels eliminating the need for separation. In some preferred embodiments, a reaction microchannel (or microchannels) contains a bulk flow path. The term "bulk flow path" refers to an open path (contiguous bulk flow region) within the reaction chamber. A contiguous bulk flow region allows rapid fluid flow through the reaction chamber without large pressure drops. Bulk flow regions within each reaction channel preferably have a cross-sectional area of $5 \times 10^{-8}$ to $1 \times 10^{-2}$ m$^2$, more preferably $5 \times 10^{-7}$ to $1 \times 10^{-4}$ m$^2$. The bulk flow regions preferably comprise at least 5%, more preferably at least 50% and in some embodiments, at least 90% of either 1) the internal volume of the reaction chamber, or 2) a cross-section of the reaction channel.

In many preferred embodiments, the microchannel apparatus contains multiple microchannels, preferably groups of at least 5, more preferably at least 10, parallel channels that are connected in a common manifold that is integral to the device (not a subsequently-attached tube) where the common manifold includes a feature or features that tend to equalize flow through the channels connected to the manifold. Examples of such manifolds are described in U.S. Published Pat. Application No. 20050087767, filed Oct. 27, 2003 which is incorporated herein as if reproduced in full below. In this context, "parallel" does not necessarily mean straight, rather that the channels conform to each other. In some preferred embodiments, a microchannel device includes at least three groups of parallel microchannels wherein the channel within each group is connected to a common manifold (for example, 4 groups of microchannels and 4 manifolds) and preferably where each common manifold includes a feature or features that tend to equalize flow through the channels connected to the manifold.

While simple microchannels can be utilized, the invention has advantages for apparatus with complex microchannel geometries. In some preferred embodiments, the microchannel apparatus includes one or more of the following characteristics: at least one contiguous microchannel has a turn of at least 45°, in some embodiments at least 90°, in some embodiments a u-bend, a length of 50 cm or more, or a length of 20 cm or more along with a dimension of 2 mm or less, and in some embodiments a length of 50-500 cm; at least 2 adjacent channels, having an adjacent length of at least one cm, are connected by plural orifices along a common microchannel wall where the area of orifices amounts to 20% or less of the area of the microchannel wall in which the orifices are located and where each orifice is 0.6 mm$^2$ or smaller, in some embodiments 0.1 mm$^2$ or smaller—this is a particularly challenging configuration because a coating should be applied without clogging the holes; or at least two, in some embodiments at least 5, parallel microchannels having a length of at least 1 cm, have openings to an integral manifold, where the manifold includes at least one dimension that is no more than three times the minimum dimension of the parallel microchannels (for example, if one of the parallel microchannels had a height of 1 mm (as the smallest dimension in the set of parallel microchannels), then the manifold would possess a height of no more than 3 mm). An integral manifold is part of the assembled device and is not a connecting tube. In some apparatus, a microchannel contains a u-bend which means that, during operation, flow (or at least a portion of the flow) passes in opposite directions within a device and within a contiguous channel (note that a contiguous channel with a u-bend includes split flows such as a w-bend, although in some preferred embodiments all flow within a microchannel passes through the u-bend and in the opposite direction in a single microchannel).

In preferred embodiments, the inventive apparatus (or method) includes a catalyst material. In preferred embodiments, the surface of the catalyst defines at least one wall of a bulk flow path through which the mixture passes. During operation, a reactant composition flows through the microchannel, past and in contact with the catalyst. In some embodiments, a catalyst is provided as an insert that can be inserted into (or removed from) each channel in a single piece. The catalyst is preferably a coating of material within a microchannel reaction channel or channels because it creates an advantageous capacity/pressure drop relationship. In a flow-by catalyst configuration, fluid preferably flows in a gap adjacent to a porous insert or past a wall coating of catalyst that contacts the microchannel wall.

Figure 2:
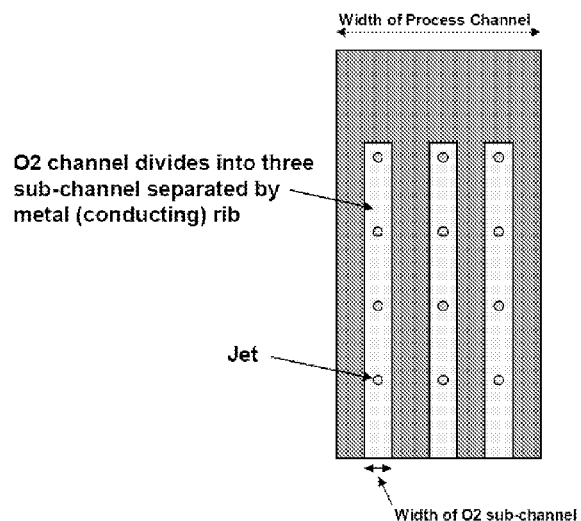
FIG. 2 is a top down view of the sheet containing the oxygen subchannels. Jet holes for passage of the oxygen into the process channel (i.e., the first section). A fuel is oxidized in the process channel to generate heat for the dehydrogenation reaction.

In some preferred embodiments, microchannel apparatus for oxidative dehydrogenation is essentially without heat exchange channels that are separate from the process/product channels for the ODH process. Examples are shown in FIGS. 1 and 2. As shown in FIG. 1, multiple sets of microchannels can be provided within a single apparatus. Preferably, the process stream in the process channel is fed into the product channel.

Figure 4:
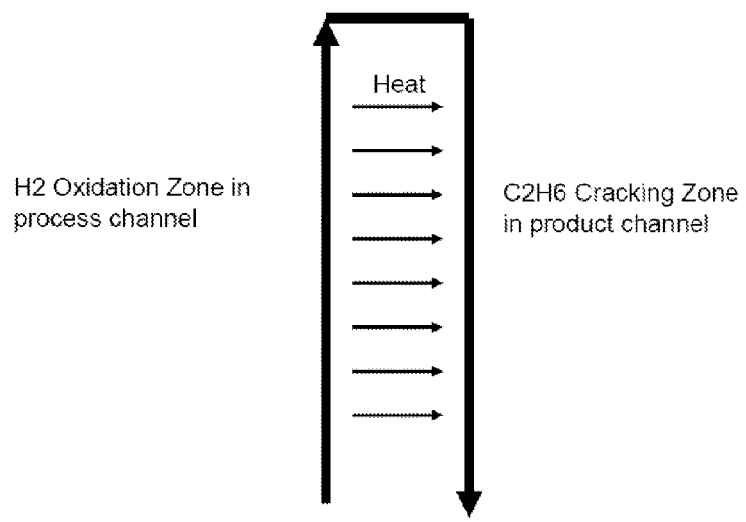
FIG. 4 is a schematic representation of heat transfer in a u-bend device.

In preferred embodiments of the present invention, there is a u-turn in the ODH process channel. In this configuration, oxidation can occur principally or entirely within the first side of the U. Heat generated in the process side then transfers across a channel wall to provide heat for the endothermic reaction that occurs in the product side. This is schematically illustrated in FIG. 4. Of course, some heat will also be convected along with the flow of the process stream. Additionally, apparatus will typically also include a recuperator section prior to the exothermic reaction section in which heat from the product stream warms a fluid stream on its way to the exothermic reaction (first) section.

Preferably, there is an ODH catalyst (not shown) in the first section (labeled "Process Channel" in FIG. 1) of the u-bend reactor. Pt alloyed with Au and/or Pd is especially preferred, and electrolessly deposited catalyst has been found to possess superior properties. The catalyst may also be in the u-bend.

Figure 5A:
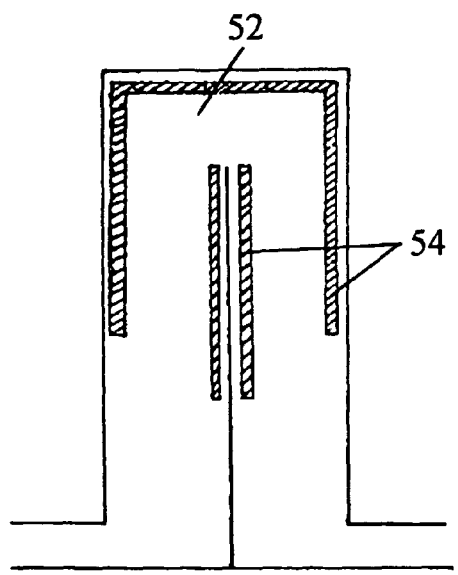
FIG. 5a schematically illustrates a simple u-bend. In this illustration, a catalyst (shaded region) is disposed on surfaces in and near the u-bend.
Figure 5B:
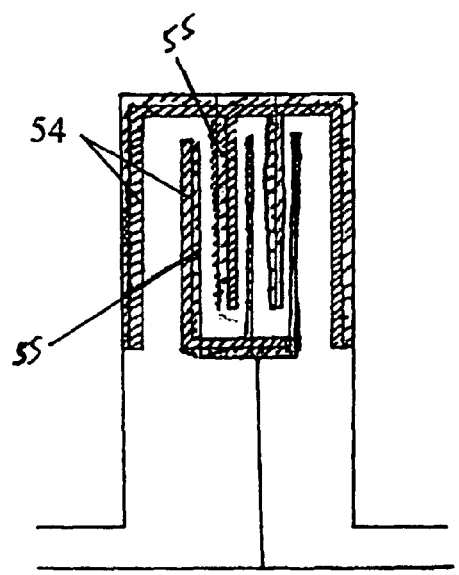
FIG. 5b schematically illustrates a u-bend modified by the addition of baffles for more surface area.

The u-bend is preferably a simple u-bend 52, meaning that it is unobstructed and contains an open, bulk flow for gas flow. The U can be rounded or have corners. In some embodiments, the u-bend can have baffles 55 (see FIG. 5b) or other structures that provide additional surfaces for catalyst 54; however, the heat generating channel(s) of the reactor should allow for fast flow of the process stream. Thus, the oxidation side is preferably unobstructed (for example, without felts, powders or other impediments to flow) and contains a wall coating and a bulk flow path; in some preferred embodiments, the product channel(s) are also unobstructed with a wall coating and a bulk flow path.

Figure 3:
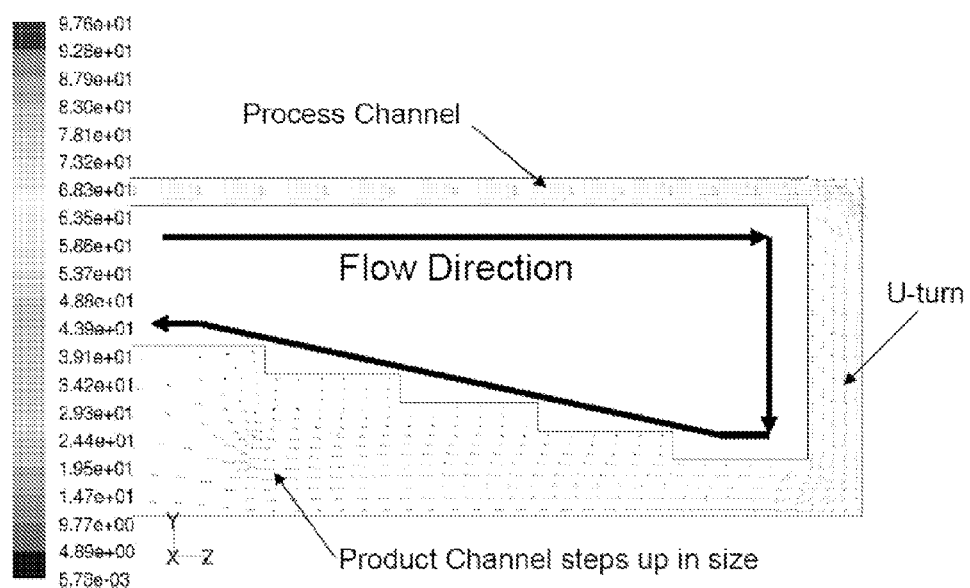
FIG. 3 shows a cross-sectional view of the region near the u-bend and illustrates how shim construction methods could be used to make steps for increasing volume of the product channel. The process stream flow path is shaded in this figure.

In some preferred embodiments, the product channel (also called the second section) has a larger cross-sectional area (and thus a larger volume) than the process channel (also called the first section). This provides additional contact time for the relatively slower dehydrogenation process. Preferably, the process channel has an essentially constant cross section that is the same size or smaller than the product channel. The product channel can increase in volume along its length (see an embodiment of this in FIG. 3 in which shims are stepped to gradually increase volume). In some preferred embodiments, the second section includes a cross-sectional area that is at least two times (in some embodiments at least 3 times and in some embodiments at least 5 times) larger than that of the first section. The length of the first section and the second section can be the same or different.

As exemplified in FIGS. 1 and 2, oxygen (or hydrogen) can be added stagewise into the process stream as it passes through the first section. Optimally, catalyst is disposed on the surface opposing the oxygen jets so that the exothermic reaction occurs on the wall for heat transfer to the cracking reaction. Oxygen should not be added to the second section.

Figure 8:
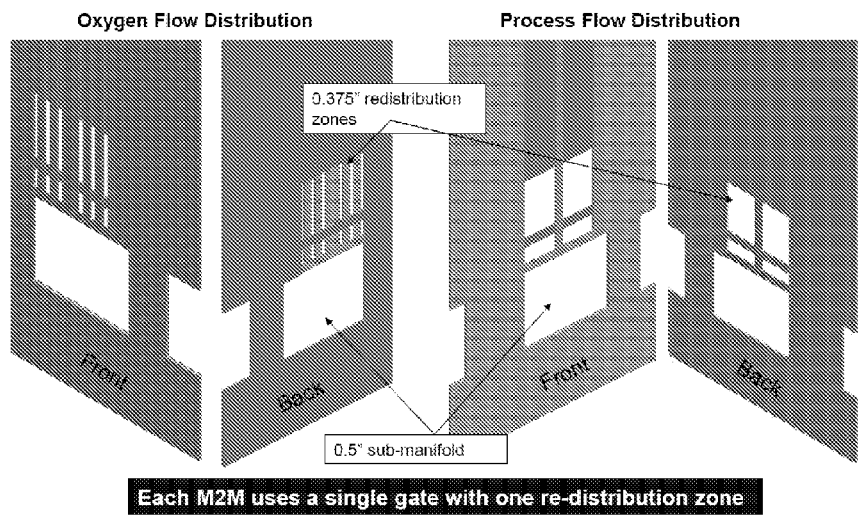
FIG. 8 shows structures that modify manifolding to equalize flow across multiple channels.

In scaled up apparatus with numerous channels, such as the multichannel reactor of FIG. 1, there are flow equalizing structures at the header connecting the microchannels with larger piping. These structures, such as shown in FIG. 8, equalize flow to plural channels throughout a device. Flow equalizing structures are known in the art. In a preferred embodiment, there are no flow equalizing structures on the footer of a multichannel device. More preferably the reactor is operated in a vertical direction with respect to gravity so that soot particles can more easily drop out of the product channel.

Apparatus Design That Minimizes Heat Transfer to Exterior

Figure 6B:
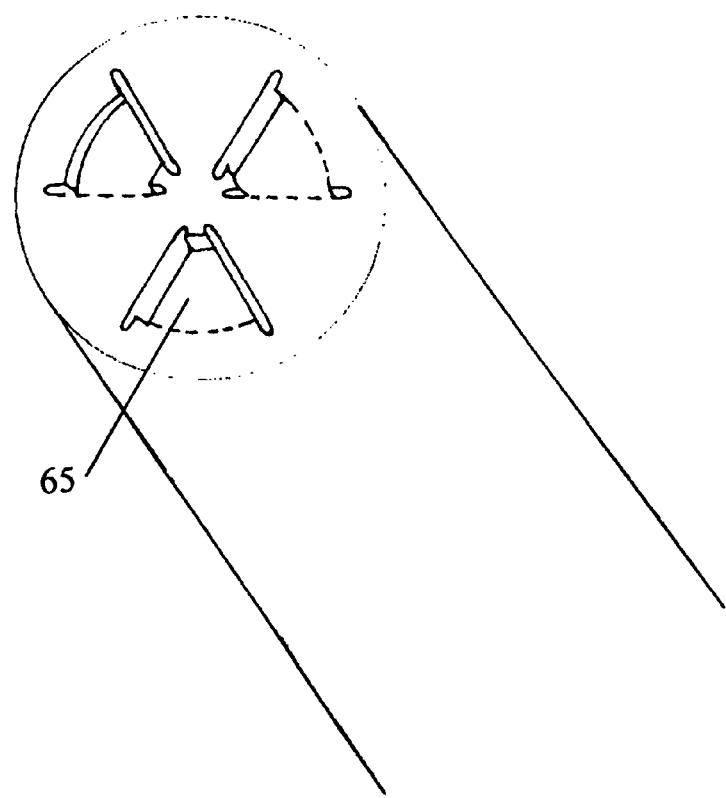
Figure 6C:
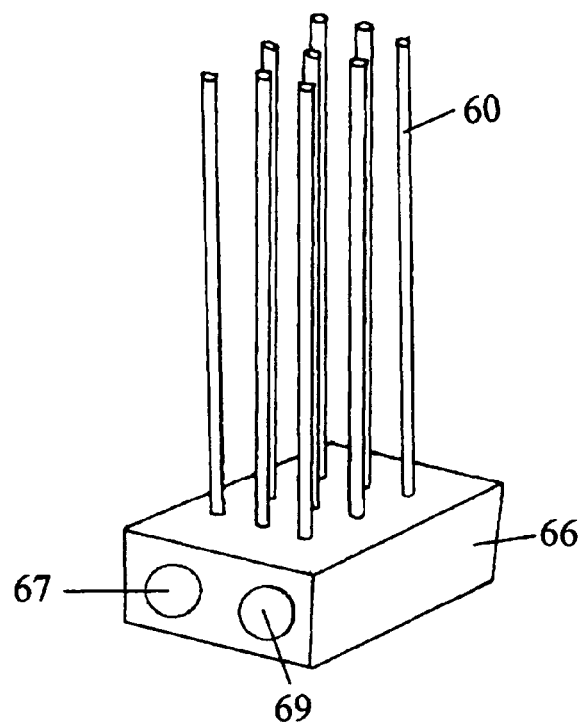

FIG. 6 illustrates apparatus that minimizes heat transfer to the exterior of a device. In this device, the device 60 has a central axis 61 and flow paths 63 radiating from the central axis. The device can be made by known processes such as stacking sheets to form a laminated device or electro-discharge machining. An open area 65 at the end of the flow paths can form a u-turn so that a process stream returns in the direction it came. Also, as shown in FIG. 6, numerous such devices can share a common manifold. In a particularly preferred embodiment, plural devices can be plugged into a single unit including both an inlet and an outlet to accommodate flow to and from the plural devices. For chemical reactions, it may be desirable for catalyst to be disposed in one or more of the flow paths. For separation processes, may be desirable for adsorbent to be disposed in one or more of the flow paths. Also, as shown in FIG. 6, plural processor bodies can be connected into a common manifold 66 with manifold inlet 67 and manifold outlet 69.

Oxidative Dehydrogenation Reactions

This invention discloses methods for the oxidative dehydrogenation of alkane(s) and/or aralkane(s) to alkene(s), alkadiene(s) and/or aralkene(s). The hydrocarbon may be any alkane or aralkane of $C_2$ up to $C_{20}$. Examples of alkane include ethane, propane, isobutane or butane or higher alkanes including up to $C_{20}$ linear and branched alkanes; examples of aralkane include ethylbenzene; examples of alkene for the purpose of this invention include ethylene, propylene and also alkadienes such as butadiene; examples of aralkene include styrene. Preferred examples of hydrocarbons are $C_2$-$C_{18}$ alkanes, preferably $C_2$-$C_{10}$ alkanes, ethylbenzene, or $C_{10}$-$C_{15}$ alkanes such as could be used for making detergent alcohols. Ethane, propane, butane and isobutane are especially preferred hydrocarbons. The alkanes can be linear, branched and cyclic. Hydrocarbons can be obtained commercially either in pure form or in mixtures. Hydrocarbons can also be derived from other reactions, and the output of these reactions used with or without an intervening purification step.

In this method, a hydrocarbon-containing mixture (the mixture is or contains a fluid and may be homogeneous or heterogeneous (for example, containing some colloidal liquid droplets or solid particulates)) flows past and/or through a catalyst material. Preferably the mixture is entirely gaseous. The mixture comprises a source of oxygen and at least one hydrocarbon; in preferred embodiments, the oxygen source is introduced immediately before the catalyst zone or within the reactor catalyst zone or, most preferably, in a staged fashion along a length of a process channel. A portion of the at least one hydrocarbon reacts to form at least one alkene and/or aralkene and the source of oxygen reacts to form water. The oxygen source is preferably dioxygen ($O_2$), and in some embodiments air is used to provide oxygen. Optionally, the product stream can be rapidly quenched to preserve products and stop further reaction to undesirable products. Quenching can be achieved using integral microchannel quench/heat exchanger to remove heat in adjacent channels to the channels through which the product is flowing. In another embodiment, the quench can be achieved by mixing the hot product stream with a cold fluid to rapidly reduce temperature. The quench fluid can be condensible fluids, for example, excess low temperature steam or a condensible hydrocarbon injected as a liquid that evaporates and cools the product stream by absorbing latent heat of evaporation from the hot product stream. Condensible fluids are attractive for use in commercial applications for gas-phase products, since they are relatively easily separated from the product mixture.

Systems of the invention can be described as including apparatus and/or catalyst in combination with reactants and/or products. Additionally, any of the individual components (such as ethane, for example) may preferably be present in at least 20% purity (based on carbon atoms), or at least 50%, or at least 90%, or 100% purity.

For autothermal ODH of an hydrocarbon (such as ethane) to an alkene (such as ethylene) or aralkene, the ethane:$H_2$ feed ratio is preferably in the range 1:0 to 1:1.5; more preferably 1:0.2 to 1:1, preferably 1:0.2 to 1:0.8, most preferably 1:0.5 to 1:0.8, and the ethane:O2 feed ratio should remain in the range 1:0.1 to 1:1, preferably 1:0.2 to 1:0.8 and most preferably 1:0.25 to 1:0.5 depending on the overall reaction selectivities and conversion.

Hydrogen in the process stream may be fed from a separate source or produced in the ODH reaction and recycled.

The reactant stream may contain diluents such as nitrogen, methane, water vapor, CO, and $CO_2$. Steam, if present in the reactant feed, is preferably present in a steam:C ratio of 5 or less, more preferably 1 or less, and in some embodiments 2 volume % or less. The total diluents to dehydrogenatable hydrocarbons molar ratio is preferably 5:1 or less, more preferably 2:1 or less, preferably less than 50 volume %, more preferably less than 20 volume % diluents in a microchannel reactor, and in some embodiments, less than 2 vol. % diluents. In some preferred embodiments, the hydrocarbons in the reactant stream are at least 75 mol %, more preferably at least 90 mol % of a single hydrocarbon (propane, for example). In some preferred embodiments, the reaction stream contains essentially no diluent.

In some embodiments of the inventive reactor or method, the reactor (or method) is configured to send the product stream into a second reactor or recycle the product stream back into the same reactor. There may be intervening separation steps to remove desired products or undesired components or separate hydrogen or a reactant or reactants. In some preferred embodiments, separation is conducted within the same integrated device as the dehydrogenation. Typically, the desired alkene or arylalkene will be separated from the product stream and the unreacted hydrocarbon portion of the product stream recycled.

A product stream containing olefins and unconverted alkanes can be used without further separation as a feedstock for other processes including alkylation. In alkylation, (typically) olefins are reacted with isoalkanes to form higher branched alkanes with high octane numbers suitable for use as components of gasoline. Where the feedstock contains isobutene, the product stream is especially suited as an alkylation feedstock since the products include C3-C5 olefins and unconverted isobutane.

In some preferred embodiments, walls of the reaction channels and/or inner surfaces of conduits and manifolds connected to the reaction channels are coated with a passivation layer. Passivation of surfaces inside the reaction chamber and/or in piping leading to, and/or especially piping leading from the reaction chamber may reduce coking and nonselective oxidation reactions and might enhance time-on-stream performance. Passivation coatings have a different composition than the underlying material. Suitable passivation coatings include a refractory oxide such as silica, alumina, zirconia, titania, chromia, ceria, Group II metals (alkaline earths) and rare earth metals, atomic numbers 57-71. The passivation coating could, optionally, be catalytic supports or could be dense coatings to protect an underlying metal wall. It is believed that surfaces may quench undesired gas phase unselective oxidations. Thus, in some embodiments, filler material such as ceramic fibers could be placed into the reaction channel in open spaces within the reaction channel that, during operation, would be occupied by hot gas.

The process channel contains an oxidative dehydrogenation catalyst. In some preferred embodiments, there is an oxidative dehydrogenation catalyst in both the process channel and the product channel, and in some preferred embodiments, there is an oxidative dehydrogenation catalyst in only the product channel. Catalyst structures within the product channel may include porous catalyst materials, monoliths, washcoats, pellets, and powders. Electroless catalyst coatings on microchannel walls are especially preferred.

In its broader aspects, a catalyst or catalysts that are known in the prior art can be used in the apparatus of the present invention. However, the ODH catalysts described above and in the examples are particularly preferred.

If necessary, the catalyst systems can be regenerated by treating the catalyst with an oxidant to oxidize reduced materials formed on or in the catalyst. Typical regeneration oxidants are oxygen or air. Catalysts can be refurbished after irreversible reduction of activity by coating the catalyst in situ with additional active materials.

In addition to the reaction microchannel(s), additional features such as microchannel or non-microchannel heat exchangers may be present. An integrated or separate heat exchanger can be used to quench the reaction products, cooling them down rapidly once the reaction has taken place to prevent further undesirable reactions of the olefins. In some embodiments of the inventive reactor or method, the reactor (or method) is configured to send the product stream into a second reactor or recycle the product stream back into the same reactor.

With microchannel reactors the high heat removal capacity makes it possible to run reactions at higher pressures and high space velocity in conventional reactors and still achieve high selectivity at high conversion. With pressures above 2 atm, preferably above 5 atm, and more preferably above 10 atm and space velocities greater than 10,000 h−1, preferably greater than 100,000 h−1, and more preferably greater than 1,000,000 h−1 it is possible to get good yields of useful products in microchannel reactors.

Preferred temperature ranges of the process of the present invention include: above 850° C.; a temperature ranging from 850 to 1050° C., more preferably above 900-1050° C., more preferably above 900° C., and in some embodiments 950-1000° C. Unless otherwise specified, "temperature" means peak temperature in the device. Alternatively, the temperature could be specified as temperature in a location such as the u-bend or second section, or as average temperature.

For operation at these temperatures, it is desirable that the internal surfaces of the reactor be covered with a passivation layer.

In some preferred embodiments, the temperature increases substantially monotonically along the length of the process channel from the start of the exothermic oxidation to the u-bend (i.e., the highest temperature is at the u-bend). "Monotonically" means in the same direction, not at the same rate. Substantially monotonic increases are shown in the examples.

Preferred pressures in the reactor are in the range of 0 to 20 bar, more preferably 0 to 8 bars. Pressures are gauge unless specified otherwise.

Gas hourly space velocity (GHSV) of the inventive methods preferably range from 1,000 h$^{-1}$ to 10,000,000 h$^{-1}$ based on reactor volume, or 1,000 ml feed/(g catalyst)(hr) to 10,000,000 ml feed/(g catalyst)(hr). In other preferred embodiments, GHSV is at least 10,000 h$^{-1}$ or at least 10,000 ml feed/(g catalyst)(hr); more preferably at least 100,000 h$^{-1}$ or at least 100,000 ml feed/(g catalyst)(hr); more preferably at least 500,000 h$^{-1}$ or at least 500,000 ml feed/g catalyst; more preferably at least 1,000,000 h$^{-1}$ or at least 1,000,000 ml feed/(g catalyst)(hr). Liquid hourly space velocity (LHSV) is preferably at least 5 h$^{-1}$; more preferably at least 20 h$^{-1}$; more preferably at least 60 h$^{-1}$; more preferably at least 100 h$^{-1}$.

Contact times in the reaction chamber are preferably are in the range of 0.001 to 5 s, more preferably less than 500 ms, more preferably less than 100 ms, and still more preferably less than about 70 ms. Volumes for determining contact times are reactor volumes in which the conditions are sufficient for either an oxidation or dehydrogenation reaction to occur; the volumes include catalyst volume (typically this volume is insignificant for an electroless plating). So, under typical ODH reaction conditions, the volume for calculating contact time typically includes the volumes of the first section, u-turn and second section. The volume would not include sections of channels where only recuperation (heat exchange) is occurring. Trivial amounts of reaction are disregarded in calculating volume.

Preferably, selectivity to carbon oxides (on a carbon atom basis) is less than 40%, more preferably less than 20%, and even more preferably less than 5%, and in some embodiments in the range of 20% and 2%.

The percent conversion of hydrocarbon (in a single pass) is preferably 50% or higher, more preferably about 60% or higher, more preferably 70% or higher, even more preferably 80% or higher, and in some embodiments in the range of 70 to about 86%. The level of percent selectivity to desired product (or products in the case where more than one valuable alkene can be formed) is preferably at least 50% more preferably at least 70%, more preferably at least 80%, and in some embodiments 80 to about 86%.

Oxygen conversions are preferably greater than 90%, more preferably greater than 95%, most prefereably greater than 99%.

EXAMPLES

Modeling Oxidative Dehydrogenation of Ethane in a Microchannel Reactor Having a U-Bend Configuration A microchannel reactor was designed to that utilized common channels to perform hydrogen oxidation and ethane cracking. The device was designed using a series of computational fluid dynamic (CFD) simulations in order to achieve an expected performance of 78% ethane conversion and 84% ethylene selectivity by using a molar feed ratio of approximately 4.5:4:1 ethane to hydrogen to oxygen, corresponding to an overall device pressure drop of less than 25 PSI.

Figure 7:
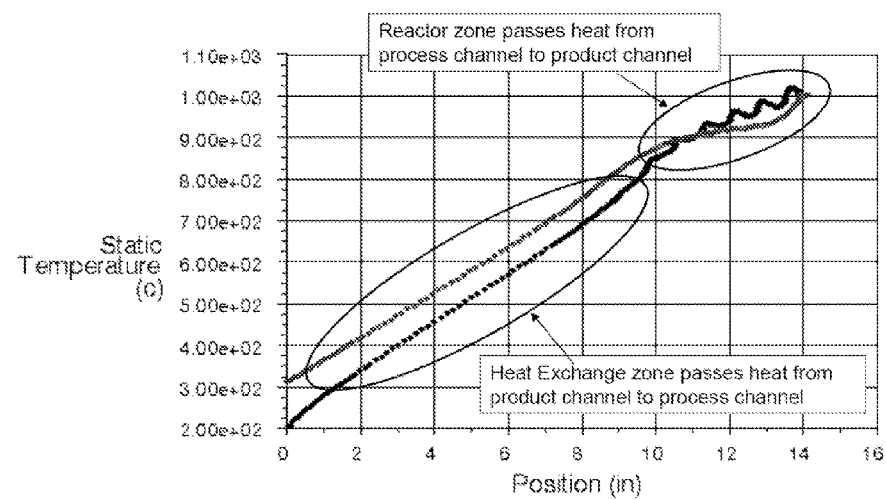
FIG. 7 is a graph from the model calculations showing temperature as a function of length for the type of device illustrated in FIGS. 1-2.

The multi-channel reactor design consists of eight identical channel sets that each includes an inlet process channel, an inlet oxygen channel and an outlet product channel (see FIG. 1). Each of the eight inlet process channels has dimensions of width equal to 0.25" and of gap equal to 0.010". Each of the eight inlet oxygen channels are subdivided into three sub-channels that overlaps and combines with a single process channel. Each of the oxygen sub-channels have dimensions of width equal to 0.03" and of gap (top to bottom height in the illustrated cross-section) equal to 0.010" and are equally spaced across the 0.25" wide process channel (see FIG. 2). The oxygen is mixed into the process channels by utilizing a staged addition process that uses a series of small circular jets ranging in diameter from 0.006"-0.010". By controlling the oxygen addition and hence the heat release, the thermal profile can be tailored to reduced internal stresses and therefore increase the life of the reactors. The oxygen is staged into the process channel over a length of 4.5" and incorporates 7 circular jets, each separated by 0.75". There is one set of seven jets for each of the oxygen sub channels and therefore there are twenty-one jets for each of the process channels. Approximately 0.5" downstream of the last staged addition point, the process channel transitions into the product channel by turning 180° through a 0.20" u-turn feature. The product channel has a width equal to 0.25" is directly overlies a single process channel. Once the gas flow has been turned (by passing through the u-turn), the product channel transitions from a gap of 0.020" up to 0.060" by going through a series of 0.010" steps that are each 0.05" long. Transitioning in this manner allows the flow to expand and reduce velocity without initiating any significant recirculation zones in the flow field (see FIG. 3). The product flow is counter to the process flow such that the heat generated from the hydrogen oxidation in the process channel can pass into the product stream to sustain the ethane cracking reaction (see FIG. 4). Once the product stream fully passes the hydrogen oxidation section, it passes heat to the process and oxygen channels along the length of a counter flow heat exchanger in order to preheat the reactants and cool the products (see FIG. 7). The product streams then exits straight out of the bottom of the device.

The eight channel sets that make up the multi-channel reactors are arranged by having four layers, each with two channel sets side-by-side. The process stream is brought in through the side of the device by four sub-manifold channels that each feed two side by side process channels. Flow distribution features have been added to ensure uniform distribution across the two channels (see FIG. 8). The oxygen stream is brought in through the side opposite from the process stream, by four sub-manifold channels that each feed six side-by-side oxygen sub channels. The flow distribution features are identical for the oxygen and process streams and each contains a 0.5" wide by 0.020" gap sub-manifold channel, a single gate that spans the feed channels, and a single 0.375" long by 0.010 gap redistribution zone that also spans the feed channels (see FIG. 8).

The multi-channel reactors can be fabricated by stacking a series of 0.010" and 0.020" thick shims between two 0.375" endplates and diffusion bonding them together. The shim sizes are ~16" by 16" such that multiple reactors can be included in one shim stack. The final bonded stack includes a total of nine devices laid out side by side. After diffusion bonding these devices are cut apart using wire EDM in order to separate the nine individual multi-channel reactors. The process and oxygen sub-manifold channels as well as the product exit channels can be opened up using plunge EDM. The main headers and footers can be welded in place. The reactor is then cleaned, aluminized, and heat treated. The catalyst solution is applied through the manifolds.

Figure 9:
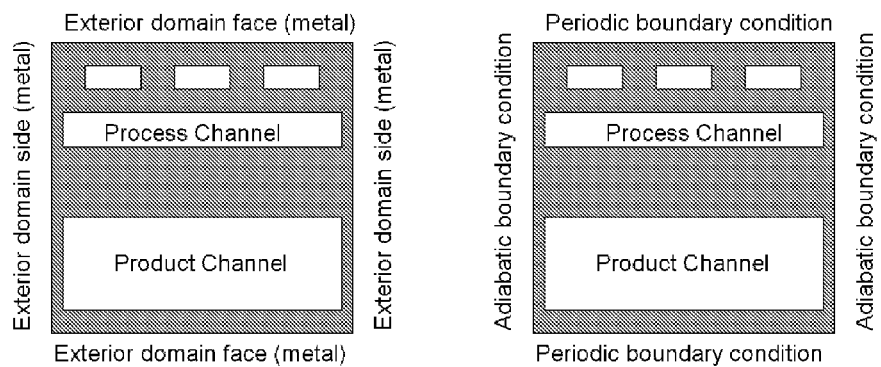
FIG. 9 is a figure labeling domains discussed in the examples.

Computational fluid dynamic (CFD) simulations were conducted to determine the staged oxygen distribution, thermal profile, predicted performance, and the sub-manifold to feed channel flow distribution quality. Two different sets of CFD models were used in these analyses. The first set of models represented a slice of the entire reactor that included 9" of heat exchange, 5" of hydrogen oxidation and 5" of ethane cracking. The model domain included a single 0.25" wide by 0.010" gap process channel, three 0.030" wide by 0.010" gap oxygen sub-channels, and a single 0.25" wide by 0.06" product channel. The oxygen and process channels were separated by a 0.010 thick shim that included a seven jet pattern for each of the three oxygen sub-channels. The process and product channels were separated by a 0.040" thick shim that included a 0.25 wide by 0.020 gap u-turn feature. The product channel included a small transition zone in which the channel gap was increased from 0.020" to 0.060" in 0.010" steps. Each step was 0.050" long. The product channel was bounded with 0.02" thick metal to created one external face of the domain and the oxygen channel was bounded by 0.020" metal to create the opposite external face of the domain. The external sides of the domain included 0.030" metal to fully enclose the channels and allow for axial conduction (see FIG. 9). The domain incorporated two types of thermal boundary conditions. The external sides the domain incorporated adiabatic boundary conditions and the external faces of the domain incorporated a periodic boundary conditions that forced both of the external domain faces to have identical temperature maps (see FIG. 9). A number of fully reactive cases were run using this type of model in order to finalize the staged oxygen addition and then to compare the predicted performance under a number of simulated conditions. Each modeled run utilized a feed ratio of 4.5:4:1 (ethane:hydrogen:oxygen) but exit pressure was varied between one atmosphere and three atmospheres and the total flow rate was varied between 10 SLPM and 30 SLPM (where total flowrate includes all of the feed gases for an entire multi-channel reactor containing eight sets of channel sets).

Figure 10:
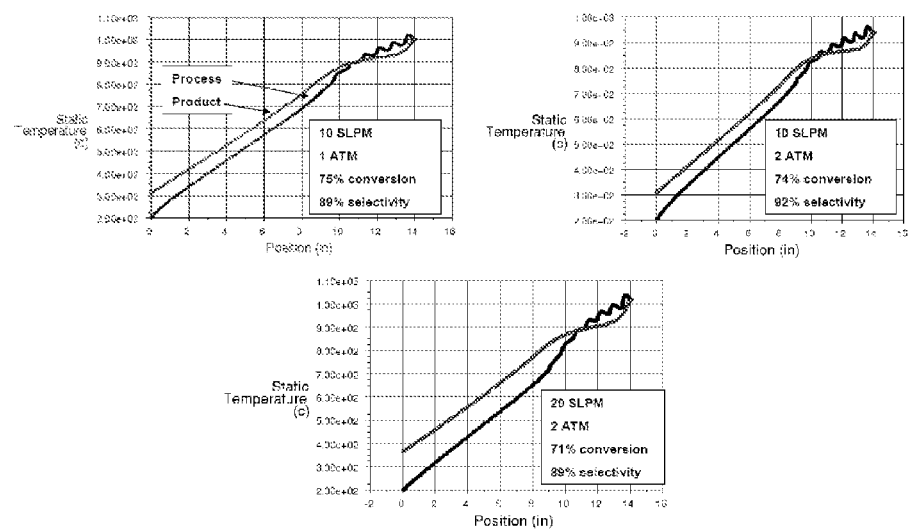
FIG. 10 are graphs from the model calculations showing temperature as a function of length for the devices described in the examples.
Figure 11:
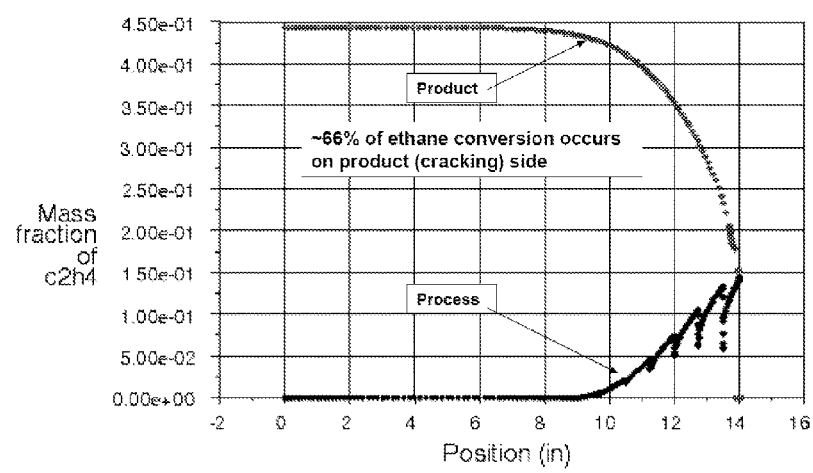
FIG. 11 shows the mass fraction of ethane in the first (process) and second (product) sections of a u-bend reactor.

The results of the simulations predict that the reactors will be able to achieve the desired ethane conversion and ethylene selectivity at the low flowrate cases (10 SLPM) and over an operational pressure range of at least 0-30 PSIG. The performance starts to suffer as the flowrate is increased. One of the reasons that the performance is reduced is due to inefficient heat exchange between the process and product streams (see table 1 and FIG. 10). Although the total ethane conversion varied for each of the runs, each simulation predicted the trend that ~⅓ of the ethane conversion occurred in the hydrogen oxidation zone (i.e. process channel) and the remaining ⅔ of the conversion occurred in the cracking zone (i.e product channel) (see FIG. 11). Furthermore, all simulations predicted that 100% of the oxygen was converted in the process channel prior to entering the u-turn. The maximum temperature predicted varied per case although generally occurred in the process channel just downstream of the last oxygen jet. The maximum metal temperature is predicted to be within the 1025° C.-1075° C. range and is dependent on the flowrate and operational pressure.

TABLE 1

Predicted Performance

| Total Flow Rate (SLPM) | Outlet Pressure (ATM) | Ethane Conversion | Ethylene Selectivity | Acetylene Selectivity | Carbon Selectivity |
|---|---|---|---|---|---|
| 10 | 1 | 74.7% | 89.5% | 1.5% | 0.5% |
| 10 | 2 | 74.2% | 92.0% | 0.9% | 0.4% |
| 20 | 2 | 71.2% | 89.2% | 1.0% | 0.6% |

Figure 12:
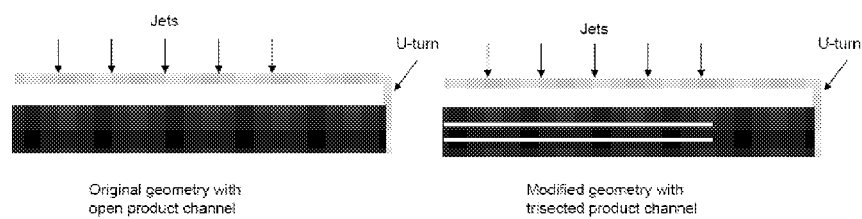
FIG. 12 shows reactor designs with a completely open product channel (black) and a product channel modified with support ribs (white), as explained in the examples.
Figure 13:
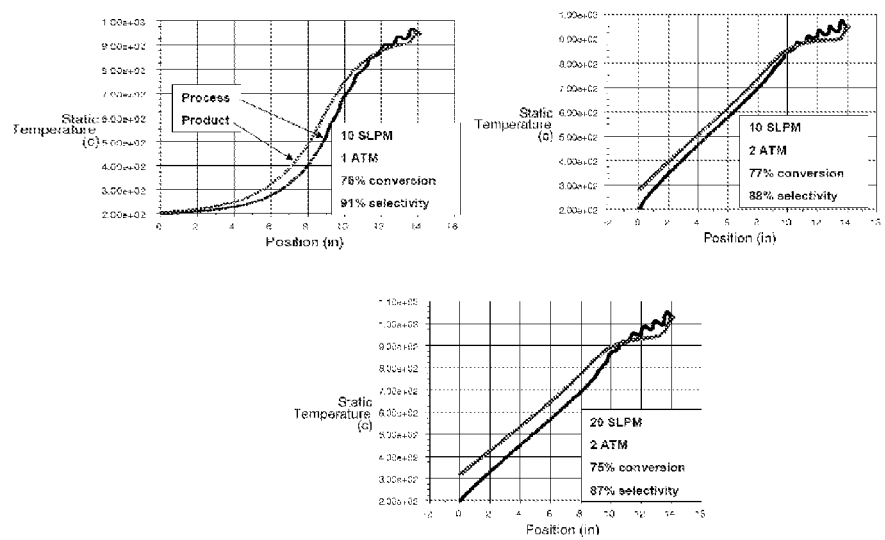
FIG. 13 are graphs from the model calculations showing temperature as a function of length for the devices described in the examples.

A second geometry was modeled that was identical to first except that the product channel was modified to include three 0.25" wide by 0.020" gap channels separated by a 0.010" thick shim instead of the open 0.060" product channel that was modeled in the first simulation set (see FIG. 12). The process channel is shaded and the flow paths in the product channel are black. The modification to the product channel was done to allow more efficient heat exchange between the process and product streams. Identical cases were run to compare the two designs. The modified design showed more efficient heat transfer and therefore outperformed the initial design at the higher flowrate conditions (see table 2 and FIG. 13). The ethane conversion and oxygen conversion showed similar trends as the initial design.

TABLE 2

Predicted Performance

| Design Type | Total Flow Rate (SLPM) | Outlet Pressure (ATM) | Ethane Conversion | Ethylene Selectivity | Acetylene Selectivity | Carbon Selectivity |
|---|---|---|---|---|---|---|
| Initial | 10 | 1 | 74.7% | 89.5% | 1.5% | 0.5% |
| Initial | 10 | 2 | 74.2% | 92.0% | 0.9% | 0.4% |

Testing of Various Pt Alloys in Microchannels for the Oxidative Dehydrogenation of Ethane to Ethylene Example 1

A coupon formed from a high temperature alloy coated with Pt-aluminide was heat-treated at 1050° C. for 10 hours prior to use. The surface of the coupon was covered with an $\alpha$-$Al_2O_3$ scale. The coupon was then put in a solution consisting of $Pt(NH_3)_4(OH)_2$, (0.2 wt % Pt) and 0.2 wt % $N_2H_4 \cdot H_2O$. The plating was performed at room temperature for 7 hours. The coupon was then cleaned with deionized water and dried in air at room temperature. Subsequently the coupon was put in a new Pt plating solution with the same composition. The plating was performed at room temperature for another 9 hours. The total Pt loading was 12 mg/in². After the plating, the coupon was calcined at 1000° C. for 4 hours in air.

The Pt plated coupon was tested in a microchannel reactor for oxidative dehydrogenation of ethane to ethylene. The reactor has two microchannels separated by the catalyst coupon. Reactants were fed at 3:2:1 ratio of ethane:hydrogen: oxygen. Catalyst entrance temperature ranged from 850 to 950° C., and contact time was fixed at 40 ms. Reaction products, i.e., ethylene, acetylene, methane, C3 (propane and propylene), C4 (butylenes, butanes and butadiene) and COx (CO and $CO_2$), were analyzed with an on-line four-column GC. The ODH performance is summarized in Table 1.

Example 2

A Pt-aluminide coupon was heat-treated at 1050° C. for 10 hours prior to use. The surface of the coupon was covered with an $\alpha$-$Al_2O_3$ scale. The coupon was then put in a solution consisting of $Pt(NH_3)_4(OH)_2$, (0.2 wt % Pt) and 0.2 wt % $N_2H_4 \cdot H_2O$. The plating was performed at room temperature for 7 hours. The Pt loading was 3.8 mg/in². Subsequently, the Pt-plated coupon was put in a Cu plating solution with $CuCl_2$ (0.4 wt % Cu), 0.6 wt % HCHO, 8 wt % $Na_4$-EDTA. The pH of the solution was adjusted to 12.3 by KOH. The plating was performed at room temperature for 11 min. The Cu loading was 6.4 mg/in² After the plating, the coupon was heat-treated at 900° C. for 4 hours in flowing $H_2$. A $PtCu_3$ alloy was formed (surface XRD analysis) after the heat-treatment.

The ODH performance is summarized in Table 1. Ethylene selectivity is increased by 8%, from 75.5% to 83.5%, at around 77% ethane conversion as compared to the Pt-plated catalyst.

Example 3

A Ni-aluminide coupon was heat-treated at 1050° C. for 10 hours prior to use. The surface of the coupon was covered with an $\alpha$-$Al_2O_3$ scale. The coupon was then put in a solution consisting of $Pt(NH_3)_4(OH)_2$, (0.2 wt % Pt) and 0.2 wt % $N_2H_4 \cdot H_2O$. The plating was performed at room temperature for 15 hours. The coupon was then cleaned with deionized water and dried in air. Subsequently the coupon was put in a new Pt plating solution with the same composition. The plating was performed at room temperature for another 0.5 hour. The total Pt loading was 8.3 mg/in². Subsequently, the Pt-plated coupon was put in an Au plating solution with $KAu(CN)_2$ (0.4 wt % Au), 0.4 wt % KCN, 1.0 wt % KOH, 2.5 wt % sodium citrate, 0.2 wt % $Na_4$-EDTA, $Pb(CH_3COO)_2$ (2 ppm Pb) and 1 wt % dimethylamine borane. The plating was performed at 80° C. for 2 hours. The Au loading was 4.2 mg/in². After the plating, the coupon was heat-treated at 900° C. for 4 hours in flowing $H_2$.

The ODH performance is summarized in Table 1. As compared to the Pt-plated catalyst, ethylene selectivity is increased by 6.7%, from 75.2% to 81.9%, at around 78.6% ethane conversion. Also no apparent deactivation was seen in 100-h on stream.

Example 4

A Ni-aluminide coupon was heat-treated at 1050° C. for 10 hours prior to use. The surface of the coupon was covered with an $\alpha$-$Al_2O_3$ scale. The coupon was then put in a solution consisting of $Pt(NH_3)_4(OH)_2$, (0.2 wt % Pt) and 0.2 wt % $N_2H_4 \cdot H_2O$. The plating was performed at room temperature for 20 hours. The Pt loading was 8.1 mg/in². Subsequently, the Pt-plated coupon was put in a Pd plating solution with 0.9 wt % $PdCl_2$, 3.4 wt % $(NH_4)_2H_2$-EDTA, 10 wt % $NH_4OH$ and 0.3 wt % $N_2H_4 \cdot H_2O$. The plating was performed at room temperature for 23 min. The Pd loading was 4.4 mg/in². After the plating, the coupon was heat-treated at 900° C. for 4 hours in flowing $H_2$.

The ODH performance is summarized in Table 1. As compared to the Pt-plated catalyst, ethylene selectivity is increased by 7.4%, from 75.6% to 83%, at around 77% ethane conversion.

Example 5

A Ni-aluminide coupon was heat-treated at 1050° C. for 10 hours prior to use. The surface of the coupon was covered with an $\alpha$-$Al_2O_3$ scale. The coupon was then put in a solution consisting of $Pt(NH_3)_4(OH)_2$, (0.2 wt % Pt) and 0.2 wt % $N_2H_4 \cdot H_2O$. The plating was performed at room temperature for 7.4 hours. The Pt loading was 5.0 mg/in². Subsequently, the Pt-plated coupon was put in a Pd plating solution with 0.9 wt % $PdCl_2$, 3.4 wt % $(NH_4)_2H_2$-EDTA, 10 wt % $NH_4OH$ and 0.3 wt % $N_2H_4 \cdot H_2O$. The plating was performed at room temperature for 11 min. The Pd loading was 2.9 mg/in². After that, the Pt—Pd plated coupon was put in an Au plating solution with $KAu(CN)_2$ (0.4 wt % Au), 0.4 wt % KCN, 1.0 wt % KOH, 2.5 wt % sodium citrate, 0.2 wt % $Na_4$-EDTA, $Pb(CH_3COO)_2$ (2 ppm Pb) and 1 wt % dimethylamine borane. The plating was performed at 80° C. for 26 min. The Au loading was 7.0 mg/in². After the plating, the coupon was heat-treated at 900° C. for 4 hours in flowing $H_2$.

The ODH performance is summarized in Table 1. As compared to the Pt-plated catalyst, ethylene selectivity is increased by 7.3%, from 75.6% to 82.9%, at around 77% ethane conversion. Also no apparent deactivation is seen in 50 hours on stream.

Example 6

A Ni-aluminide coupon was heat-treated at 1050° C. for 10 hours prior to use. The surface of the coupon was covered with an $\alpha$-$Al_2O_3$ scale. The coupon was then put in a solution consisting of $Pt(NH_3)_4(OH)_2$, (0.2 wt % Pt) and 0.2 wt % $N_2H_4 \cdot H_2O$. The plating was performed at room temperature for 22 hours. The Pt loading was 8.9 mg/in². The coupon was then cleaned with deionized water and dried in air at room temperature. Subsequently the coupon was put in a new Pt plating solution with the same composition. The plating was performed at room temperature for another 1.5 hours. The total Pt loading was 11 mg/in² Next, the Pt-plated coupon was put in a Pd plating solution with 0.9 wt % $PdCl_2$, 3.4 wt % $(NH_4)_2H_2$-EDTA, 10 wt % $NH_4OH$ and 0.3 wt % $N_2H_4 \cdot H_2O$. The plating was performed at room temperature for 5 min. The Pd loading was 2.5 mg/in². After the plating, the coupon was heat-treated at 900° C. for 4 hours in flowing $H_2$.

The ODH performance is summarized in Table 1. As compared to the Pt-plated catalyst, ethylene selectivity is increased by 3.7%, from 75.6% to 79.3%, at around 78% ethane conversion.

Example 7

A Ni-aluminide coupon was heat-treated at 1050° C. for 10 hours prior to use. The surface of the coupon was covered with an $\alpha$-$Al_2O_3$ scale. The coupon was then put in a solution consisting of $Pt(NH_3)_4(OH)_2$, (0.2 wt % Pt) and 0.2 wt % $N_2H_4 \cdot H_2O$. The plating was performed at room temperature for 7 hours. The Pt loading was 5.0 mg/in². Subsequently, the Pt-plated coupon was put in an Au plating solution with KAu(CN)$_2$ (0.4 wt % Au), 0.4 wt % KCN, 1.0 wt % KOH, 2.5 wt % sodium citrate, 0.2 wt % Na$_4$-EDTA, Pb(CH$_3$COO)$_2$ (2 ppm Pb) and 1 wt % dimethylamine borane. The plating was performed at 80° C. for 1 hour. The Au loading was 8.0 mg/in$^2$. After the plating, the coupon was heat-treated at 900° C. for 4 hours in flowing H$_2$.

The ODH performance is summarized in Table 1. As compared to the Pt-plated catalyst, ethylene selectivity is increased by 4.6%, from 75.6% to 80.2%, at around 77% ethane conversion.

TABLE 1

ODH performance of electroless plated Pt-alloy catalysts

| Example | Catalyst | T (° C.) | Conversion (%) | | Selectivity (%) | | | | | | C balance (%) |
|---|---|---|---|---|---|---|---|---|---|---|---|
| | | | C$_2$H$_6$ | O$_2$ | C$_2$H$_4$ | CH$_4$ | COx | C$_2$H$_2$ | C3 | C4 | |
| 1 | Pt on PtAl | 850 | 71.3 | 94.9 | 76.2 | 7.3 | 11.8 | 0.6 | 2.4 | 1.7 | −0.8 |
| | 12 mg/in$^2$ | 865 | 76.5 | 95.2 | 75.6 | 7.7 | 11.9 | 0.9 | 2.1 | 1.8 | −1.9 |
| | | 875 | 78.7 | 96.5 | 75.2 | 7.8 | 12.0 | 1.1 | 2.0 | 1.9 | −0.6 |
| | | 885 | 82.7 | 96.8 | 73.7 | 8.4 | 12.1 | 1.5 | 1.8 | 2.1 | −1.2 |
| 2 | Pt—Cu (1:5) on PtAl | 890 | 72.6 | 99.6 | 85.1 | 5.1 | 4.2 | 1.7 | 1.5 | 2.3 | 0.5 |
| | 10 mg/in$^2$ | 902 | 77.4 | 99.8 | 83.6 | 5.4 | 4.2 | 2.3 | 1.5 | 3.0 | 0.7 |
| | | 910 | 80.7 | 99.5 | 82.4 | 5.8 | 4.0 | 2.8 | 1.4 | 3.7 | 0.2 |
| 3 | Pt—Au (2:1) on NiAl | 890 | 66.5 | 98.7 | 83.1 | 5.3 | 6.7 | 1.2 | 1.7 | 2.0 | 0.4 |
| | 12.5 mg/in$^2$ | 905 | 73.8 | 99.2 | 82.1 | 5.9 | 6.0 | 1.8 | 1.6 | 2.6 | 0.7 |
| | | 915 | 78.6 | 99.4 | 81.9 | 6.1 | 4.7 | 2.5 | 1.5 | 3.3 | −4.2 |
| | | 930 | 86.5 | 99.4 | 78.3 | 7.1 | 4.2 | 3.8 | 1.3 | 5.3 | −3.1 |
| 4 | Pt—Pd (1:1) on NiAl | 910 | 66.3 | 99.7 | 85.6 | 4.3 | 3.7 | 2.5 | 1.6 | 2.3 | −3.0 |
| | 12.5 mg/in$^2$ | 930 | 77.0 | 99.7 | 83.0 | 5.2 | 3.4 | 3.5 | 1.5 | 3.4 | −3.0 |
| | | 940 | 82.0 | 99.8 | 81.3 | 5.8 | 3.3 | 4.2 | 1.5 | 3.9 | −3.8 |
| 5 | Pt—Pd—Au (1:1:1.4) on NiAl | 925 | 59.8 | 99.8 | 86.1 | 4.5 | 3.3 | 2.3 | 1.4 | 2.4 | 0.9 |
| | 14.9 mg/in$^2$ | 928 | 77.5 | 100.0 | 82.9 | 5.1 | 2.2 | 4.1 | 1.4 | 4.3 | 0.9 |
| | | 935 | 80.1 | 99.8 | 81.7 | 5.4 | 2.2 | 4.5 | 1.4 | 4.8 | 1.0 |
| | | 950 | 85.1 | 99.8 | 79.1 | 6.0 | 2.0 | 5.5 | 1.3 | 6.1 | 1.5 |
| 6 | Pt—Pd (5:1) on NiAl | 865 | 61.6 | 97.4 | 81.3 | 5.7 | 9.1 | 0.4 | 1.9 | 1.6 | −2.6 |
| | 13.5 mg/in$^2$ | 875 | 65.2 | 98.5 | 81.8 | 5.8 | 8.1 | 0.7 | 1.8 | 1.8 | −1.6 |
| | | 900 | 78.4 | 99.1 | 79.3 | 7.1 | 7.5 | 1.8 | 1.6 | 2.7 | −1.6 |
| | | 915 | 83.8 | 99.3 | 77.4 | 7.7 | 7.6 | 2.4 | 1.4 | 3.5 | 0.7 |
| 7 | Pt—Au (0.6:1) on NiAl | 865 | 68.5 | 96.6 | 82.4 | 5.9 | 7.8 | 0.9 | 1.9 | 1.1 | 1.0 |
| | 13 mg/in$^2$ | 875 | 73.2 | 97.3 | 81.2 | 6.3 | 8.1 | 1.2 | 1.8 | 1.4 | 0.8 |
| | | 885 | 77.4 | 98.5 | 80.2 | 6.6 | 8.1 | 1.5 | 1.7 | 1.8 | 0.5 |
| | | 895 | 80.9 | 99.1 | 79.1 | 6.9 | 8.0 | 2.0 | 1.6 | 2.4 | 0.4 |

Reaction conditions: 3:2:1 ratio of ethane:hydrogen:oxygen, and 40 ms contact time.

We claim:

1. A method for oxidatively dehydrogenating a hydrocarbon, comprising:
    passing a process stream comprising an oxygen source and a hydrocarbon into a microchannel in a first section of a microchannel reactor,
    wherein, in the first section, the oxygen reacts with a fuel to generate heat;
flowing the process stream through a u-bend and into a second section;
    wherein the process stream in the first section and a process stream in a second section are separated by a thermally conductive wall;
    wherein heat from the reaction with oxygen in the first section passes through the thermally conductive wall and into the process stream in the second section; and
    removing hydrogen from the hydrocarbon to form a product and hydrogen; and
    wherein more of the product is formed in the second section than in the first section.

2. The method of claim 1 wherein hydrocarbon conversion in the first section is 30% or less.

3. The method of claim 1 wherein the product is formed with an overall conversion of at least 70% and an overall selectivity of 80%, and wherein contact time of the process stream in the microchannel reactor is 100 ms or less.

4. The method of claim 3 wherein the peak temperature is 1050° C. or less.

5. The method of claim 3 wherein the peak temperature is 1000° C. or less.

6. The method of claim 1 wherein the first section, in a region where the oxygen source reacts with the fuel to generate heat, comprises a first cross-sectional area;
    wherein the second section comprises a second cross-sectional area; and
    wherein the second cross sectional area is at least twice as large as the first cross-sectional area.

7. The method of claim 1 wherein the hydrocarbon is selected from the group of ethane, propane and isobutane; wherein hydrogen flows into the first section; wherein the oxygen source comprises dioxygen; and wherein at least 99% of the dioxygen is consumed in the first section.

8. A method for oxidatively dehydrogenating a hydrocarbon, comprising:
    passing a process stream comprising an oxygen source and a hydrocarbon into a microchannel in a first section of a microchannel reactor,
    wherein, in the first section, the oxygen reacts with a fuel to generate heat;
flowing the feed stream through a u-bend and into a second section;
    wherein the first section, in a region where the oxygen source reacts with the fuel to generate heat, comprises a first cross-sectional area;
    wherein the process stream in the first section and a process stream in a second section are separated by a thermally conductive wall;

wherein heat from the reaction with oxygen in the first section passes through the thermally conductive wall and into the process stream in the second section; and in the second section, the hydrocarbon reacts to form a product and hydrogen;

wherein the second section comprises a second cross-sectional area; and wherein the second cross sectional area is at least twice as large as the first cross-sectional area.

9. The method of claim 8 wherein at least 70% of the hydrocarbon is converted, and the selectivity to an alkene or aralkene is at least 80%; and wherein the flow rate is controlled so that the contact time of the process stream is 100 ms or less.

10. The method of claim 9 wherein the first section, u-bend and second section each comprise an unobstructed bulk flow path.

11. The method of claim 9 wherein the first section comprises a wall coating of a Pt alloy catalyst; wherein the alloy catalyst further comprises Au or Pd; and wherein the levels of hydrocarbon conversion and selectivity are maintained for at least 100 hours of continuous operation without regeneration.

12. The method of claim 8 wherein more of the product is formed in the second section than in the first section.

13. The method of claim 8 wherein the first section comprises a wall coating of a Pt alloy catalyst; wherein the alloy catalyst further comprises Au or Pd.

14. The method of claim 8 wherein the second cross sectional area is at least three times as large as the first cross-sectional area;

and wherein a flow path is continuous through the first section, into and through the u-bend and into and through the second section;

wherein the continuous flow path comprises a transitional region from the first cross-sectional area to the second cross-sectional area, wherein the transitional region comprises an increasing cross-sectional area that increases in cross-sectional area from the first cross-sectional area to the second cross-sectional area, and the transitional region does not contain any region in which the flow path increases in cross-sectional area by three times or more over a length less than 0.6 cm, except that, if the transitional region includes a u-bend, there can be a region within 1 cm of the u-bend in which the flow path increases in cross-sectional area by three times or more over a length less than 0.6 cm.

15. A method for oxidatively dehydrogenating a hydrocarbon, comprising:

passing a process stream comprising an oxygen source and a hydrocarbon into a microchannel in a first section of a microchannel reactor, wherein the microchannel reactor comprises a continuous flow path through the first section, into and through a second section;

wherein, in the first section, the oxygen source reacts with a fuel to generate heat;

wherein the first section, in a region where the oxygen source reacts with the fuel to generate heat, comprises a first cross-sectional area;

passing the process stream from the first section into the second section;

wherein, in the second section, the hydrocarbon reacts to form an alkene or aralkene and hydrogen;

wherein the second section comprises a second cross-sectional area;

wherein the second cross sectional area is at least three times as large as the first cross-sectional area; and wherein the continuous flow path comprises a transitional region from the first cross-sectional area to the second cross-sectional area, wherein the transitional region comprises an increasing cross-sectional area that increases in cross-sectional area from the first cross-sectional area to the second cross-sectional area, and the transitional region does not contain any region in which the flow path increases in cross-sectional area by three times or more over a length less than 0.6 cm, except that, if the transitional region includes a u-bend, there can be a region within 1 cm of the u-bend in which the flow path increases in cross-sectional area by three times or more over a length less than 0.6 cm.

16. The method of claim 15 wherein the process stream is essentially without diluents.

17. The method of claim 15 wherein the transitional region includes a u-bend, and wherein there is a region within 1 cm of the u-bend in which the flow path increases in cross-sectional area by three times or more over a length less than 0.6 cm.

18. The method of claim 15 wherein the transitional region does not contain any region in which the flow path increases in cross-sectional area by three times or more over a length less than 0.6 cm.

19. A method for oxidatively dehydrogenating a hydrocarbon, comprising:

passing a process stream comprising an oxygen source and a hydrocarbon into one of the at least two flow paths of apparatus comprising:

a processor body having a length and comprising a central axis and at least two flow paths along a length of the processor body and radiating out from the center axis wherein, in a direction perpendicular to length, each of the at least two flow paths have a cross section that is substantially rectangular;

and further wherein the one of the at least two flow paths comprises an ODH catalyst.

20. The method of claim 19 further comprising a ubend in the apparatus so that the process stream returns in the same direction it came.

21. A method for oxidatively dehydrogenating a hydrocarbon, comprising:

passing a process stream comprising an oxygen source and a hydrocarbon into a microchannel in a first section of a microchannel reactor, wherein, in the first section, the oxygen source reacts with a fuel source to generate heat;

flowing the feed stream through a u-bend and into a second section;

wherein the first section comprises a Pt alloy catalyst wherein the Pt alloy comprises Au or Pd as an alloying element;

wherein the process stream in the first section and a process stream in a second section are separated by a thermally conductive wall;

wherein heat from the reaction with oxygen in the first section passes through the thermally conductive wall and into the process stream in the second section; and in the second section, removing hydrogen from the hydrocarbon to form a product and hydrogen.

22. The method of claim 21 wherein the Pt alloy catalyst is an electrolessly applied wall coating.

23. The method of claim 21 wherein the first section, in a region where the oxygen source reacts with the fuel to generate heat, comprises a first cross-sectional area;

wherein the second section comprises a second cross-sectional area; and wherein the second cross sectional area is at least twice as large as the first cross-sectional area.

24. The method of claim 23 wherein the second cross sectional area is at least three times as large as the first cross-sectional area;

and wherein a flow path is continuous through the first section, into and through the u-bend and into and through the second section; and wherein the continuous flow path comprises a transitional region from the first cross-sectional area to the second cross-sectional area, wherein the transitional region comprises an increasing cross-sectional area that increases in cross-sectional area from the first cross-sectional area to the second cross-sectional area, and the transitional region does not contain any region in which the flow path increases in cross-sectional area by three times or more over a length less than 0.6 cm, except that, if the transitional region includes a u-bend, there can be a region within 1 cm of the u-bend in which the flow path increases in cross-sectional area by three times or more over a length less than 0.6 cm.

25. A method for oxidatively dehydrogenating a hydrocarbon, comprising:

passing an oxygen source and a hydrocarbon into a microchannel at a temperature of at least 850° C.;

wherein the microchannel comprises an electroless plating of a Pt alloy catalyst wherein the Pt alloy comprises Au or Pd as an alloying element;

controlling flow rate such that the contact time is 100 ms or less;

wherein at least 70% of the hydrocarbon is converted to products and wherein selectivity to alkene or aralkene is at least 80%; and maintaining conversion and selectivity at these levels for at least 100 hours without performing a decoking step or a catalyst regeneration step.

26. The method of claim 25 wherein the peak temperature is 1050° C. or less.

27. The method of claim 25 wherein the Pt alloy catalyst comprises Au as an alloying element.

28. The method of claim 25 wherein the hydrocarbon consists essentially of ethane, and wherein hydrogen gas also flows through the microchannel.

29. The method of claim 28 wherein the hydrocarbon conversion is at least about 77%.

30. The method of claim 25 wherein the hydrocarbon conversion is at least about 80%.

* * * * *